US010369289B2

(12) United States Patent
Cabiri et al.

(10) Patent No.: US 10,369,289 B2
(45) Date of Patent: Aug. 6, 2019

(54) PATCH INJECTOR WITH SLIDABLE JOINT

(71) Applicant: West Pharma. Services IL, Ltd., Ra'anana (IL)

(72) Inventors: Oz Cabiri, Macabim-Reut (IL); Paul H. Norton, St. Augustine, FL (US); Ran Hezkiahu, Herzliya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 15/766,437

(22) PCT Filed: Oct. 10, 2016

(86) PCT No.: PCT/US2016/056227
§ 371 (c)(1),
(2) Date: Apr. 6, 2018

(87) PCT Pub. No.: WO2017/062935
PCT Pub. Date: Apr. 13, 2017

(65) Prior Publication Data
US 2018/0311440 A1 Nov. 1, 2018

Related U.S. Application Data

(63) Continuation of application No. 15/204,542, filed on Jul. 7, 2016, and a continuation of application No.
(Continued)

(51) Int. Cl.
*A61M 5/31* (2006.01)
*A61M 5/142* (2006.01)
(Continued)

(52) U.S. Cl.
CPC ............ *A61M 5/28* (2013.01); *A61M 5/3134* (2013.01); *A61M 5/3202* (2013.01);
(Continued)

(58) Field of Classification Search
CPC ............ A61M 5/14248; A61M 5/3204; A61M 5/1456
See application file for complete search history.

(56) References Cited

U.S. PATENT DOCUMENTS

| 1,125,887 A | 1/1915 | Schimmel |
| 5,275,582 A | 1/1994 | Wimmer |

(Continued)

FOREIGN PATENT DOCUMENTS

| DE | 855313 C | 11/1952 |
| EP | 2364739 A1 | 9/2011 |

(Continued)

OTHER PUBLICATIONS

Office Action dated Oct. 2, 2018 in JP Application No. 2018-535062 (Year: 2018).*

(Continued)

*Primary Examiner* — Rebecca E Eisenberg
*Assistant Examiner* — Tasnim Mehjabin Ahmed
(74) *Attorney, Agent, or Firm* — Panitch Schwarze Belisario & Nadel LLP

(57) ABSTRACT

An injector including at least one fluid reservoir having a needle, a surface attached to skin and coupled to the fluid reservoir by at least a first joint and a second joint at least a portion of one of the joints being slidable or having interlocking arms. At least a portion of a path of translation of a slidable portion of the first joint and a portion of a path of translation of the second joint are angled in respect to each another.

26 Claims, 9 Drawing Sheets

Related U.S. Application Data

15/269,248, filed on Sep. 19, 2016, now Pat. No. 10,086,145.

(60) Provisional application No. 62/281,536, filed on Jan. 21, 2016, provisional application No. 62/284,806, filed on Oct. 9, 2015.

(51) Int. Cl.
*A61M 5/158* (2006.01)
*A61M 5/28* (2006.01)
*A61M 5/32* (2006.01)
*A61M 5/34* (2006.01)
*A61M 5/145* (2006.01)

(52) U.S. Cl.
CPC ............ *A61M 5/3204* (2013.01); *A61M 5/34* (2013.01); *A61M 5/1456* (2013.01); *A61M 5/14248* (2013.01); *A61M 2005/1581* (2013.01); *A61M 2005/312* (2013.01); *A61M 2005/341* (2013.01); *A61M 2207/00* (2013.01)

(56) References Cited

U.S. PATENT DOCUMENTS

| | | | |
|---|---|---|---|
| 5,858,001 | A | 1/1999 | Tsals et al. |
| 6,186,982 | B1 * | 2/2001 | Gross ............... A61M 5/14248 604/132 |
| 6,189,292 | B1 | 2/2001 | Odell et al. |
| 6,500,150 | B1 | 12/2002 | Gross et al. |
| 6,719,141 | B2 | 4/2004 | Heinz et al. |
| 6,824,529 | B2 | 11/2004 | Gross et al. |
| 6,843,782 | B2 | 1/2005 | Gross et al. |
| 7,967,795 | B1 | 6/2011 | Cabiri |
| 8,603,028 | B2 | 12/2013 | Mudd et al. |
| 8,721,603 | B2 | 5/2014 | Lundquist |
| 2005/0154353 | A1 | 7/2005 | Alheidt |
| 2005/0245956 | A1 | 11/2005 | Steinemann et al. |
| 2009/0093792 | A1 | 4/2009 | Gross et al. |
| 2013/0253434 | A1 | 9/2013 | Cabiri |
| 2013/0296824 | A1 | 11/2013 | Mo et al. |
| 2014/0148784 | A1 | 5/2014 | Anderson et al. |
| 2014/0163526 | A1 | 6/2014 | Cabiri et al. |
| 2014/0194854 | A1 | 7/2014 | Tsals |
| 2015/0157806 | A1 | 6/2015 | Knutsson |

FOREIGN PATENT DOCUMENTS

| | | |
|---|---|---|
| JP | 2006507067 A | 3/2006 |
| JP | 2014515669 A | 7/2014 |
| WO | 9721457 A1 | 6/1997 |
| WO | 2005070485 A1 | 8/2005 |
| WO | 2009043000 A1 | 4/2009 |
| WO | 2011110872 A1 | 9/2011 |
| WO | 2012145752 A2 | 10/2012 |
| WO | 2013036602 A1 | 3/2013 |
| WO | 2015048791 A1 | 4/2015 |
| WO | 2015118358 A1 | 8/2015 |
| WO | 2016087626 A1 | 6/2016 |
| WO | 2016087627 A1 | 6/2016 |

OTHER PUBLICATIONS

Translation of Office Action dated Oct. 2, 2018 in JP Application No. 2018-535062 (Year: 2018).*
Int'l Preliminary Report on Patentability dated Jan. 18, 2018 in Int'l Application No. PCT/US2016/056227.
Int'l Search Report and Written Opinion dated Dec. 8, 2016 in Int'l Application No. PCT/US2016/056227.
Written Opinion dated Sep. 11, 2017 in Int'l Application No. PCT/US2016/056227.
Office Action dated Oct. 2, 2018 in JP Application No. 2018-535062.

* cited by examiner

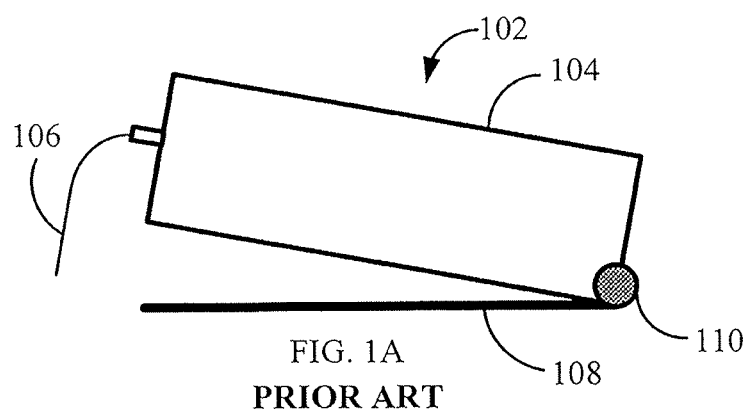
FIG. 1A
PRIOR ART
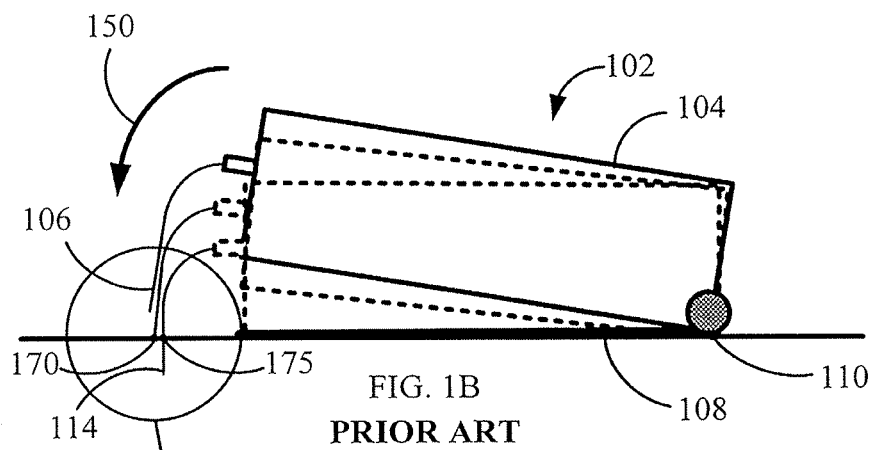
FIG. 1B
PRIOR ART
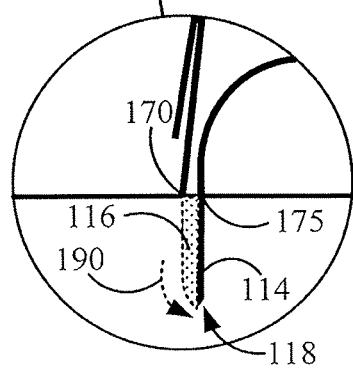
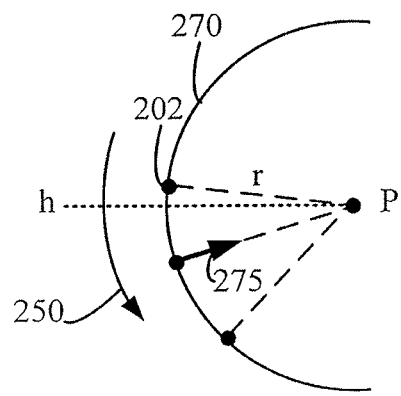
FIG. 2
PRIOR ART

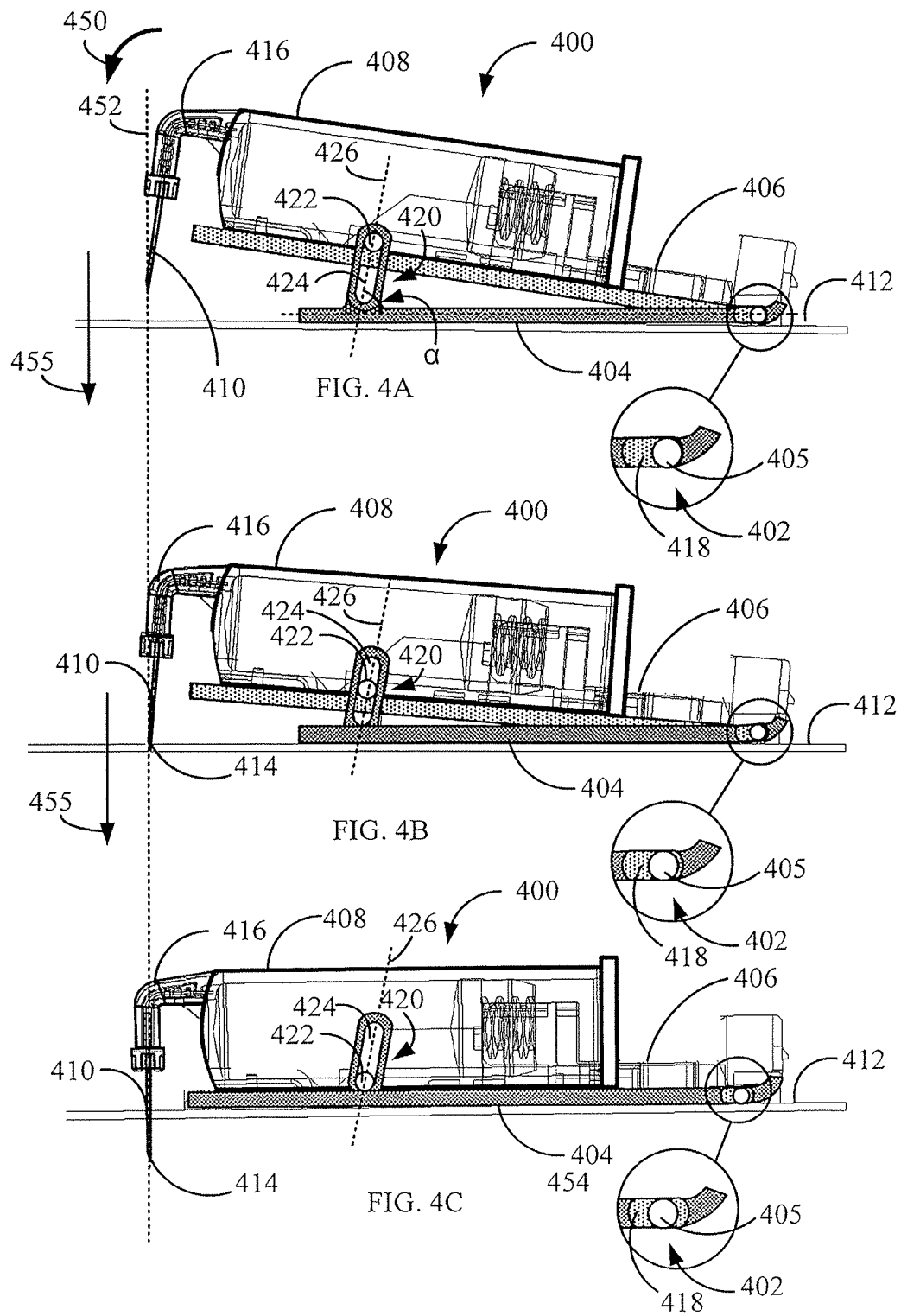

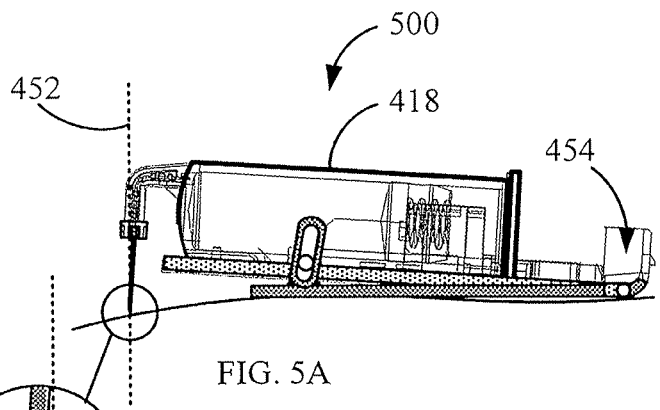
FIG. 5A
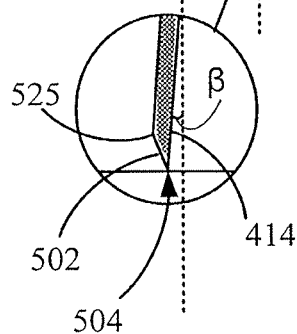
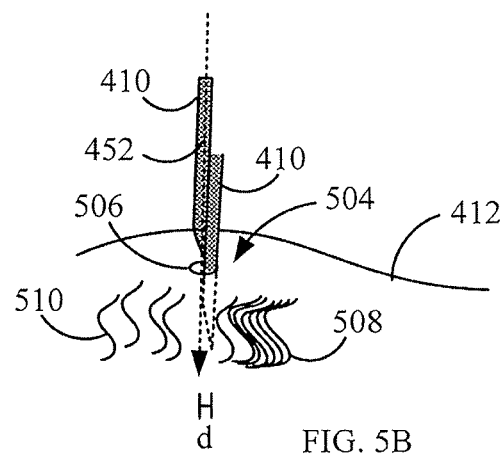
FIG. 5B
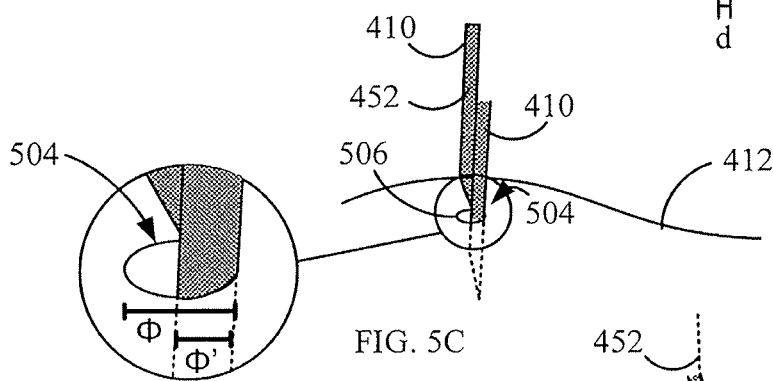
FIG. 5C
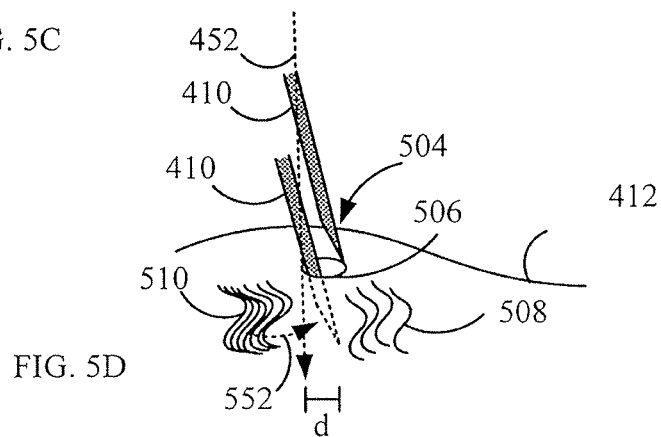
FIG. 5D

PATCH INJECTOR WITH SLIDABLE JOINT

CROSS-REFERENCE TO RELATED APPLICATION

This application is a section 371 of International Application No. PCT/US16/56227, filed Oct. 10, 2016, which was published Apr. 13, 2017 under International Publication No. WO 2017/062935 A1, which is a continuation of U.S. application Ser. No. 15/204,542, filed Jul. 7, 2016, which claims the benefit of U.S. Provisional Application No. 62/281,536, filed Jan. 21, 2016 and U.S. Provisional Application 62/284,806, filed Oct. 9, 2015; and a continuation of U.S. application Ser. No. 15/269,248, filed Sep. 19, 2016, the disclosures of which are incorporated herein by reference.

FIELD AND BACKGROUND OF THE INVENTION

The present invention, in some embodiments thereof, relates to a self-injector and, more particularly, but not exclusively, to a patch self-injector.
A subcutaneous (SC) injection is a method of administering medication under the skin, commonly into fatty tissue between the skin and the muscle. The current trend toward subcutaneous injection for biologicals using auto-injectors such as, for example, reusable and disposable pens, auto-injectors, and patch injectors that adhere to the surface of the skin gives users the freedom to self-inject at home.

In many cases, reformulated drugs can be more concentrated, at times more viscous and the desired injection volume greater than 1 mL. For high viscosity products, delivery in under 10 seconds can lead to painful injections, which may result in users failing to follow their treatment regimen. It may be difficult at times for a user to keep a Pen or any other upright injector stationary and at a correct angle of injection during injections for periods of over 10 seconds or several minutes. Patch auto or self-injectors for self-administered SC injections are therefore becoming more common.

Additional background art includes U.S. Pat. Nos. 6,843,782 and 5,858,001.

SUMMARY OF THE INVENTION

According to an aspect of some embodiments of the present invention there is provided an injector including one or more fluid reservoirs having a needle, a surface attached to skin and coupled to the fluid reservoir by one or more first joint and a second joint one or more portions of one of the joints being slidable.

According to some embodiments of the invention one or more portion of a path of translation of the slidable portion of the first joint and a portion of a path of translation of the second joint are angled in respect to each another and one or more portion of the path of translation of the portion of the second joint restricts the one or more portion of the path of translation of the portion of the first joint.

According to some embodiments of the invention, one or more portion of the path of translation of the second joint is curved. According to some embodiments of the invention one or more portion of the path of translation of the second joint is sinusoidal. According to some embodiments of the invention, one or more portion of the path of translation of the second joint is serpentine.

According to some embodiments of the invention, one or more of the joints has at least two degrees of freedom in respect to the surface, one or more being a rotational degree of freedom both degrees of freedom being on a same plane. When the fluid reservoir is rotated in respect to the surface, one or more portion of a path of travel of one or more portion of the needle defined by at least the two degrees of freedom crosses a surface of the skin along a straight line. According to some embodiments of the invention, the portion is the proximal edge of a bevel of the needle. According to some embodiments of the invention, a tilt angle of the needle is generally parallel to the straight path. According to some embodiments of the invention, the needle forms an entry hole in skin with a diameter ($\Phi$) being twice the diameter ($\Phi'$) of the needle.

According to some embodiments of the invention, when the fluid reservoir is rotated in respect to the surface, one or more portion of a path of travel of one or more portion of the needle defined by at least the two paths of translation crosses a surface of the skin along a straight line. According to some embodiments of the invention, one or more of the paths translation is parallel to the skin and the needle travels along a path one or more portion of which is defined by a combination of the rotational degree of freedom and the translational degree of freedom.

According to some embodiments of the invention, the needle travels along a path one or more portion of which is defined by one or more of the rotational degree of freedom and the translational degree of freedom. According to some embodiments of the invention, the portion is a tip of the needle. According to some embodiments, the portion is the upper end of a bevel of the needle.

According to some embodiments of the invention, at least the two degrees of freedom define a path of travel at which one or more portion of the needle crosses the surface of the skin angled at less than 3 degrees in respect to the straight line. According to some embodiments of the invention, the portion is a tip that includes a beveled opening facing forward (away from the body of the fluid reservoir) and one or more portion of the needle is tangential to a curve defined by the rotational degree of freedom. According to some embodiments of the invention, one or more portion of the needle is normal to a radius of a curve defined by the rotational degree of freedom.

According to some embodiments of the invention, one or more of the joints includes one or more pin-in-slot hinge. According to some embodiments of the invention, one or more slot is oriented parallel to the surface of the skin. According to some embodiments of the invention, one or more of the first and second joints is located between the back end (non-needle end) and front end (needle end) of the injector.

According to some embodiments of the invention, the fluid reservoir further includes one or more angled head and plunger coupled to a tip of the head and wherein one or more of the joints includes one or more slotted cylinder coupled to the surface and sized and fitted to slidingly accommodate the angled head and the plunger.

According to some embodiments of the invention, one or more portion of the needle is resilient. According to some embodiments of the invention, one or more portion of the needle is curved. According to some embodiments of the invention, one or more joint includes one or more groove and one or more protrusion slidingly accommodated within the groove. According to some embodiments of the invention, one or more joint includes an elastic member.

According to an aspect of some embodiments of the present invention there is provided an injector, including one or more fluid reservoir having a needle, a surface attached to skin and coupled to the fluid reservoir by one or more first joint and a second joint one or more joint including at least two interlocking arms. According to some embodiments of the invention, one or more of the interlocking arms is pivotly coupled to the surface. According to some embodiments of the invention, the interlocking arms are pivotly coupled to each other.

According to an aspect of some embodiments of the present invention there is provided a method of injection, including rotating a needle of a fluid reservoir in respect to a surface of skin, concurrently moving the needle along a translational degree of freedom and inserting one or more portion of the needle across the surface of skin along a straight line. According to some embodiments of the invention, inserting one or more portion of the needle across the surface of skin angled at less than 3 degrees from the straight line. According to some embodiments of the invention, the translational degree of freedom is axial in respect to the skin. According to some embodiments of the invention, the movement in the translational degree of freedom is a in a back and forth direction. According to some embodiments of the invention, the concurrently rotating and moving the needle includes adjusting a path of travel and/or angle of tilt of a needle entering the skin. According to some embodiments of the invention, further including minimizing backpressure on a bevel of the needle to a backpressure of between 80-85% of the backpressure before adjustment. According to some embodiments of the invention, further including forming an entry hole in skin with a diameter ($\Phi$) being twice the diameter ($\Phi'$) of the needle.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEW OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A and 1B are cross section view simplified illustrations of a self-injector as known in the art;

FIG. 2 is a simplified diagram of formation of a curvilinear path by a tangential point connected to a rotation point via a fixed-length radius;

FIGS. 4A, 4B and 4C are side-view simplified illustrations of operative stages of an exemplary embodiment of a self-injector;

FIGS. 5A, 5B, 5C, 5D and 5E are side view, simplified illustrations of a self-injector needle and the effect of the joint on needle angle at penetration of the needle into skin;

DESCRIPTION OF SPECIFIC EMBODIMENTS OF THE INVENTION

Figure 3A:
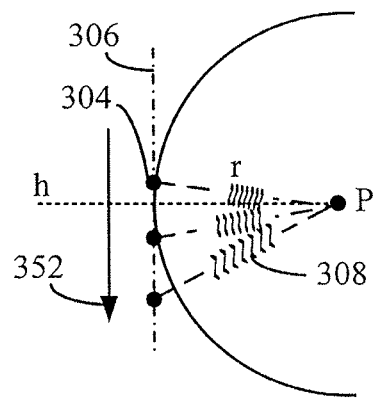
FIGS. 3A, 3B and 3C are simplified diagrams of optional joints that convert a curvilinear path of travel of a tangential point connected to a point of rotation via a radius to a substantially straight path of motion.

The present invention, in some embodiments thereof, relates to self-injectors and, more particularly, but not exclusively, to a patch self-injector.

An aspect of some embodiments of the invention relates to a self-injector having at least two joints connecting at least a portion of a surface attached to skin and a fluid reservoir, at least a portion of one of the joints being slidable in respect to other portion of joint. In some embodiments, at least one joint comprises a sliding joint. In some embodiments, the path of translation of the second joint restricts the path of translation of the portion of the first joint. In some embodiments, the restriction depends on an angle between the paths of translation. In some embodiments the angle is a sharp angle. In some embodiments the angle is less than 90 degrees. In some embodiments, paths of translation of the two joints are on the same plane.

In some embodiments, the fluid reservoir is a syringe. In some embodiments, the fluid reservoir is a cartridge. In some embodiments, the fluid reservoir is a vial.

In some embodiments, the joint comprises at least one slot. In some embodiments, the joint comprises at least one rail. In some embodiments, the joint comprises at least one groove. In some embodiments, the joint comprises at least one sleeve. In some embodiments, the sleeve is positioned about the needle. In some embodiments, the sleeve comprises at least one slot. In some embodiments, the fluid reservoir and frame are slidable in respect to each other. In some embodiments, at least one joint comprises at least two interlocking arms.

In some embodiments, at least one joint is disposed at the back end (non-needle end) of the injector. In some embodiments, at least one joint is disposed at the front end (needle end) of the injector. In some embodiments at least one joint is disposed between the back end (non-needle end) and front end (needle end) of the injector. In some embodiments, the angle of penetration of the injection needle changes while maintaining the point of entry into the skin. In some embodiments, the injection needle moves concurrently along at least two planes changing its angle of penetration in respect to the path of travel while maintaining the point of entry into the skin.

In some embodiments, at least one of the joints comprises a planar joint. In some embodiments, at least one of the joints comprises a non-planar joint. In some embodiments, the joint injector comprises both a planar joint and a non-planar joint. In some embodiments, at least portions of the joint planar joint and non-planar joint are on the same plane, the plane being normal to the axis of rotation. In some embodiments, the planar joint and non-planar joint are not on the same plane, the plane being normal to the axis of rotation. In some embodiments, the planar joint comprises a pin-in-slot joint. In some embodiments, at least one joint has one degree of freedom. In some embodiments, the joint has two degrees of freedom. In some embodiments, the joint has more than two degrees of freedom. In some embodiments, the joint has at least one axial linear degree of freedom. In some embodiments, the joint has at least one rotational degree of freedom and one axial degree of freedom. In some embodiments the rotational degree of freedom and the axial linear degree of freedom are on the same plane. In some embodiments, at least one joint prevents swivel motion of the frame and fluid reservoir in respect to each other, about a swivel axis normal to the axis of rotation.

An aspect of some embodiments of the invention relates a self-injector having at least two joints connecting at least a portion of a surface attached to skin and a fluid reservoir one or more of the joints comprises at least two degrees of freedom in respect to the surface, at least one being a rotational degree of freedom. In some embodiments, both degrees of freedom are on a same plane. In some embodiments, the plane is normal to the skin.

An aspect of some embodiments of the invention relates to a path of travel of at least a portion of a needle of a fluid reservoir defined by at least two joints connecting at least a portion of a surface attached to skin and a fluid reservoir with the needle. In some embodiments, one or more of the joints comprises at least two degrees of freedom in respect to the surface, at least one being a rotational degree of freedom. In some embodiments, a path of travel of at least a portion of the needle defined by the two degrees of freedom crosses a surface of the skin along a straight line.

An aspect of some embodiments of the invention relates to a path of travel at which a fluid reservoir needle crosses the surface of skin along a straight line and angled at less than 3 degrees in respect to the straight line. In some embodiments, the angle of penetration of at least a portion of a needle of a fluid reservoir is defined by at least two joints connecting at least a portion of a surface attached to skin and a fluid reservoir with the needle. In some embodiments, one or more of the joints comprises at least two degrees of freedom in respect to the surface, at least one being a rotational degree of freedom. In some embodiments the needle comprises a beveled tip. In some embodiments the bevel at the needle tip faces forward (away from the fluid reservoir). In some embodiments, the needle is curved.

For purposes of better understanding some embodiments of the present invention, as illustrated in FIGS. 3-8 of the drawings, reference is first made to the construction and operation of an auto-injection device as illustrated in FIGS. 1A and 1B, collectively referred to as FIG. 1, which are cross section simplified illustrations of a self-injector as known in the art.

As shown in FIG. 1A, self-injector 102 comprises a fluid reservoir 104 and a needle 106, orientated generally normal to the longitudinal axis of fluid reservoir 104. Fluid reservoir 104 is rotatingly coupled to a base 108 via a hinge 110 that is fixed in place, i.e., immovable from its fixed location. In operation and as shown in FIG. 1B, base 108 is placed against a surface 112 of the skin and fluid reservoir 104 is rotated about hinge 110 in a direction indicated by arrow 150 bringing needle 106 to penetrate surface 112 of the skin at a point of entrance 170.

Upon insertion of needle 106 into the skin, tip 114 of needle 106 follows a curvilinear path indicated by arrow 190 a component of which is an inwardly radial component of movement (see also FIG. 2) directed towards the axis of rotation of the fluid reservoir. Inwardly directed radial movement of needle tip 114 may, in some instances, stretch and possibly tear tissue 116 in the wake of curvilinear path 190 between point of entry 170 and a final resting point 175. As shown in FIG. 1B, tip 114 comprises a beveled opening 118 facing the body of the fluid reservoir or axis of rotation to which it is attached. Along the curvilinear path 190 of needle tip 114 between point of entry 170 and a final resting point 175 tissue may be forced into opening 118 and clog needle tip 114.

FIG. 2 is a simplified diagram that demonstrates formation of a curvilinear path such as path 290 of FIG. 1B. In FIG. 2 a tangential point 202 is connected to a point of rotation (P) via a fixed-length radius (r). Point of rotation (P) is fixed in place, i.e., immovable from its location. When point 202 is moved in a direction indicated by arrow 250 crossing a horizon (h), fixed-length radius (r) and fixed-in-place point of rotation (P) restrict point 202 movement to a curvilinear path 270. Movement along curvilinear path 270 may include an inwardly radial component 275 of movement, directed towards point of rotation (P). In some cases, point 202 may represent tip 114 of needle 106 and horizon (h) may represent surface 112 of the skin.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 3B:
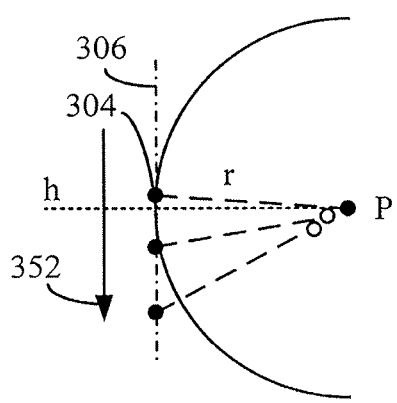

In some self-injectors there is importance to the shape of the path along which the injection needle travels. As explained above, a needle penetrating tissue substantially along a straight (linear) path of travel, minimizing inwardly radial component 275 of movement, may, in some cases, possibly lessen tissue damage such as excessive tissue stretch and possibly tear (e.g., 116, FIG. 1B) along the path of travel through the tissue. As explained above, FIGS. 3A and 3B, collectively referred to as FIG. 3, are simplified diagrams that demonstrate optional mechanisms that convert a path of travel of a tangential point connected to a point of rotation (P) via a radius (r) from a curvilinear path to a substantially straight (linear) path of motion and minimize inwardly radial component 275 of movement. In some embodiments, the tangential point comprises a portion of a needle, the needle being perpendicular to radius (r).

In some embodiments, curvilinear movement of a tangential point 304 from above horizon (h) to below horizon (h) may be converted into linear movement in a direction indicated by arrow 352 along a tangential straight path 306. In some exemplary embodiments shown in FIG. 3A, radius (r) comprises at least one elastic member 308, e.g., a spring that allows radius (r). In some embodiments, elastic member 308 may be a linear elastic member. In some embodiments, elastic member 308 stretches to maintain point 304 on path 306. Alternatively and optionally, in some exemplary embodiments, shown in FIG. 3B, radius (r) has a fixed length and point of rotation (P) is allowed to move closer to path 306 as necessary to maintain point 304 on path 306.

Figure 3C:
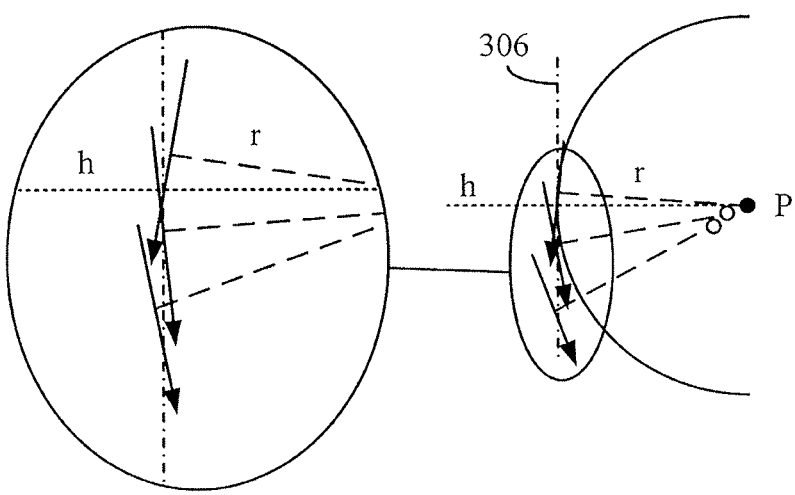

In the examples shown in FIGS. 3A, 3B and 3C, which are diagrammatic illustrations of spatial orientations of a needle travelling along a path tangential to a circle, point 304 may represent a tip of a needle and horizon (h) may represent surface 112 of the skin. In some examples, a limiting factor, for example, resistance of elastic member 308 (FIG. 3A) or a physical barrier may restrict translation of point 304 to path 306.

On a smaller scale, and as shown in FIG. 3C, and is explained in greater detail elsewhere in this disclosure, in some instances due to mechanical limitations, joints (e.g., the joints mechanism of operation illustrated in FIGS. 3A and 3B) may eliminate inwardly radial component 275 of movement of a tip of a needle travelling along path 306. However and as shown in FIG. 3C, the body of a needle may rotate slightly while travelling along straight path 306 and the tip of the needle (tangential point 403) may still minutely deviate from path 306. In some examples, a limiting factor, for example, resistance of elastic member 308 (FIG. 3A) or a physical barrier may maintain the angle of needle at point of crossing horizon (h) at less than 3 degrees from path 306. As shown in FIGS. 3A-3C and explained in greater detail elsewhere in the disclosure, in some embodiments, point of rotation (P) comprises a joint that has two or more degrees of freedom in respect to a surface attached to skin, at least one being a rotational degree of freedom. In some embodiments, both degrees of freedom are on a same plane. In some embodiments, the plane is normal to the skin. In some embodiments, the translational degree of freedom defines a straight line. In some embodiments, the translational degree of freedom is parallel to said skin.

As explained elsewhere in this disclosure, user discomfort from an injection may be brought about by mainly the nature of the path along which a needle penetrates the skin and the angle of the needle relative to the path of penetration at which it enters the skin. For example, a needle penetrating skin along a curvilinear path (see also 1B) may rupture skin and subcutaneous tissue causing discomfort to the user. Additionally or alternatively, a needle excessively angled in respect to a straight path of penetration of skin may cause discomfort to a user as well.

Reference is now made to FIGS. 4A, 4B and 4C, collectively referred to as FIG. 4, which are side-view simplified illustrations depicting three successive operative stages of an exemplary embodiment of a self-injector during introduction of a needle thereof into skin. In some embodiments, self-injector 400 is a patch self-injector adhered to the surface of the skin of a user. In some embodiments, the self-injector comprises at least one joint 402/420 that couples surface 404 and a fluid reservoir 408 with at least one needle 410. In some embodiments, frame 404 is attached to skin of a user. In some embodiments, surface 404 comprises a frame. In some embodiments, joint 402/420 has at least one degree of freedom. In some embodiments, joint 402/420 has at least two or more degrees of freedom in respect to surface 404. In some embodiments, at least one of the degrees of freedom is a rotational degree of freedom, for example, rotating fluid reservoir 408 about joint 402/420 bringing needle 410 to cross the surface of skin 412 and penetrate skin 412. In some embodiments, both degrees of freedom are on a same plane normal to skin 412. In some embodiments, at least one degree of freedom comprises translational freedom of movement, for example, moving fluid reservoir 408 and needle 410 optionally axially, in a back and forth direction [i.e., in a direction from the back end (non-needle end) towards the front end (needle-end) of injector 400 and vice versa].

In the exemplary embodiment of FIG. 4 a fluid reservoir 408 is supported by a support plate 406 fitted to support at least fluid reservoir 408 and at least one needle 410. In an exemplary embodiment, self-injector 400 comprises one or more joints 402/420 rotatingly connecting support plate 406 and frame 404. Joint 402 of the embodiment depicted in FIG. 4 comprises at least one first pin 405, attached to support plate 406 and slidably engages frame 404 via an elongated slot 418 in frame 404. Elongated slot may be in a form of a straight line, a curved line, a serpentine line, a sinusoidal line or any geometrical form calculated to bring needle 410 to travel in a straight line and enter the surface of skin 412 at a properly adjusted tilt angle (β) as described elsewhere in the disclosure. In some embodiments, elongated slot 418 is oriented longitudinally, parallel to the long axis of frame 404, long axis of fluid reservoir 408 and surface 412 of the skin, providing first pin 405 with freedom to move, optionally axially, in a back and forth direction [i.e., in a direction from the back end (non-needle end) towards the front end (needle-end) of injector 400 and vice versa]. In some embodiments, pin 405 and elongated slot 418 form a pin-in-slot joint parallel to the long axis of frame 404 on a plane normal to surface 412 of the skin. In some embodiments, pin 405 and elongated slot 418 form a pin-in-slot joint parallel to the long axis of frame 404 on a plane parallel to surface 412 of the skin.

In some embodiments, support plate 406 is fitted to support at least one fluid reservoir 408 having at least one needle 410 projecting from fluid reservoir 408 angled neck 416. In some embodiments, at least a portion of needle 410 is normal to the longitudinal axis of fluid reservoir 408. In some embodiments, at least a portion of needle 410 is normal to the support plate 406.

In the exemplary embodiment showed in FIG. 4, rotation of support plate 406 about joint 402 in respect to frame 404 and in a direction indicated by arrow 450 brings about co-rotation of fluid reservoir 408 supported thereby, moving needle 410 towards surface 412 of the skin. In some embodiments, joint 402 supports forward [i.e., from the back end (non-needle end) towards the front end (needle-end) of injector 400] and backward, optionally axial, movement of fluid reservoir 408 in respect to frame 404.

In some embodiments injector 400 comprises at least a second joint 420 including a second pin 422 attached to support plate 406 and slidably engages frame 404 via an elongated slot 424 in frame 404. In some embodiments, joint 420 restricts the forward and backward, optionally axial movement of joint 402. The level of restriction depends on the angle (α) between paths of translation of joints 402 and 420. In FIG. 4, the paths of translation are defined by elongated slots 418/424 in each of joints 402/420 respectively. In the exemplary embodiment of FIG. 4, elongated slot 424 is oriented along a forwardly declining slope 426 at an angle (α) between 40 and 90, 50 and 80, 60 and 70 degrees more than 90 or less than 40 or intermediate angles between paths of translation of joints 402 and 420. As support plate 406 is rotated about joint 402 in respect to frame 404, elongated slot 424 guides pin 422 along slope 426, which in turn pulls, optionally axially, support plate and first pin 405 forwardly up to a limit defined by angle (α).

Forward movement of support plate 406 and fluid reservoir 408 concurrently with rotation of support plate 406 and fluid reservoir 408 supported thereby in respect to frame 404 contributes to conversion of curvilinear movement of angled neck 416 on the front end (needle-end) of fluid reservoir 408 to linear, tangential movement of needle tip 414 as explained elsewhere in this disclosure. As shown in FIGS. 4A, 4B and 4C, which represent successive stages in introduction of needle tip 414 into the skin as support plate 406 and fluid reservoir 408 continue to be rotated, optionally from an elevated angular state to a final horizontal state parallel to surface 412 of the skin, needle tip 414 travels along a path defined by at least two degrees of freedoms discussed elsewhere in the disclosure and approaches and eventually penetrates surface 412 of the skin. Optionally, needle tip 414 moves along a tangential straight path 452, similar to path 306 of FIGS. 3A and 3B in a direction indicated by arrow 455.

A potential advantage of the combined action of joints 402/420 is in the formation of a straight path of travel of needle tip 414 through surface 412 of the skin and reducing discomfort to a user during introduction of the needle into the skin.

Figure 5E:
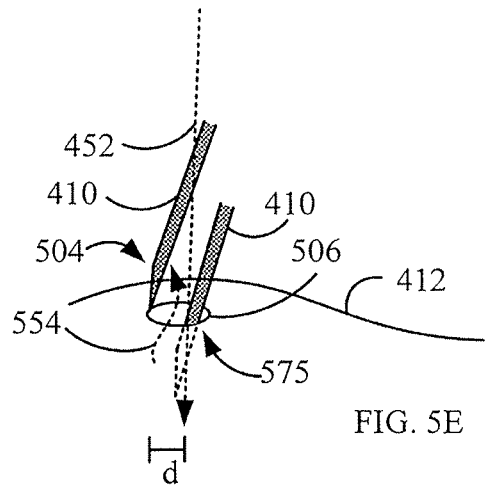

Reference is now made to FIGS. 5A, 5B, 5C, 5D and 5E, collectively referred to as FIG. 5, which are side view, simplified illustrations of a needle 410 tip 414 demonstrating the effect of an exemplary embodiment of a joint such as that depicted in FIG. 3 on angle of needle at a point of penetration of tip 414 into skin 412.

As described elsewhere in this disclosure, in some embodiments, joints 402/420 may not only reduce inwardly radial component 275 of movement of a tip of a needle but also compensate for a tilt or angle of the body of needle 410 relative to straight path of travel 306. The smaller the angle (β) the less the discomfort experienced by a user at introduction of needle 410 into the skin. As shown in FIG. 5A, in some embodiments, needle 410 is angled at an angle (β). In some embodiments, angle (β) may be less than 5 degrees, less than 3 degrees, less than 1 degree, more than 5 degrees or an intermediate angle in respect to straight path 452.

In some embodiments, an angle (β) of needle 410 in respect to straight path 452 brings needle tip 414 to minutely deviate from straight path 452. In FIGS. 5A-5E, tip 414 may minutely deviate from path 452 by a distance of deviation (d) due to a change in the angle of the needle in reference to path of travel 452. In some embodiments distance of deviation (d) is measured between point of entry 504 of needle tip 414 into the surface 412 of the skin to the final resting position 506 of tip 412 in the Subcutaneous tissue.

Optionally, to avoid possible clogging of needle opening (as discussed elsewhere in this disclosure) and generation of high back pressure, in some embodiments, a beveled opening 502 of the needle tip 414 faces forward (i.e., away from the body of the fluid reservoir to which it is attached).

FIG. 5B illustrates an exemplary embodiment, in which joints 402/420 are adjusted properly bringing the tilt angle of needle 410 close to parallel to path 452, resulting in minimal deviation (d) of needle tip 414 from path 452 and creating an optimally sized entry hole 506 in surface 412 of the skin. Movement of needle tip 414 from point of entry 504 to final resting position 575 compresses tissue 508 behind (i.e., on the side of fluid reservoir 418 body) of tip 414 and stretches tissue 510 ahead (i.e., on the side away from fluid reservoir 418 body) and away from tip 414 opening 502 reducing occurrence of back pressure resisting injection and occlusion of needle tip 414 opening.

In some embodiments and as shown in FIG. 5C, when the tilt angle (β) of needle 410 is adjusted properly it forms an optimally sized entry hole 506 upon arrival at its final resting position 575 in the injection site, having a diameter (Φ) which is between 1.5 and 2.5 times the diameter (Φ') of needle 410 e.g., Φ=1.5Φ', Φ=2Φ', Φ=2.25Φ', Φ=2.35Φ', Φ=2.5Φ' or an intermediate multiplier.

A potential advantage of an optimally sized entry hole 506 is in that pain associated with tearing of the surface of the skin is minimal and the small diameter of the opening in the surface of the skin throughout the injection period minimizes chances of leakage of an injectable being injected up to and outside the surface of the skin. In some embodiments and as depicted in FIG. 5D, overcompensation of joints 402/420 (i.e., excessive forward movement of joint 402) may bring needle 414 to tilt excessively backwards (i.e., sloping towards body of fluid reservoir 418), compressing tissue 510 ahead (i.e., on the side away from fluid reservoir 418 body) of tip 414 and stretching tissue 508 behind (i.e., on the fluid reservoir 418 body side) of tip 414 increasing occurrence of back pressure resisting injection and occluding needle tip 414 opening of bevel 502 as indicated by arrow 552.

In some embodiments and as depicted in FIG. 5E, under compensation of joints 402/420 (i.e., insufficient forward movement of joint 402) may bring needle 414 to tilt excessively forwards (i.e., sloping away from body of fluid reservoir 418), stretching surface 412 of the skin and enlarging a hole 512 created by penetration of skin 412. A large penetration hole may allow injected material to leak out of the injection site as depicted by arrow 554.

In some embodiments, joints 402/420 are oriented so that at least the proximal (upper) end 525 (FIG. 5A) of bevel 502 follows straight linear path 452. In some embodiments, joints 402/420 are oriented so that at least the central longitudinal axis of needle 410 follows straight linear path 452. Once a crossing point between path 452 and surface 412 of the skin (i.e., point of entry 504 of needle tip 414 into the surface 412 of the skin) is known, joints 402/420 may be set so that forward movement of at least portions of joints 402/420/808 maintain needle 410 tip 412 on path 452 and keeps angle of needle 410 as parallel as possible to path 452 bringing tip 412 to enter surface 412 of skin at desired point of entry 504.

A potential advantage of the combined action of at least joints 402/420 is in the formation of a straight path of travel of needle tip 414 through surface 412 of the skin, keeping angle of needle 410 as parallel as possible to the path of travel and reducing discomfort to a user during introduction of the needle into the skin.

The smaller the angle (β) the less the discomfort experienced by a user at introduction of needle 410 into the skin. In some embodiments, distance of deviation (d) of needle tip 414 from path 452 resulting from tilt of needle 410 is between 0.1 mm-1.0 mm, 0.2 mm-0.5 mm, 0.3 mm-0.4 mm, less than 0.1 mm, more than 1.0 mm or any intermediate distance.

Figure 5F:
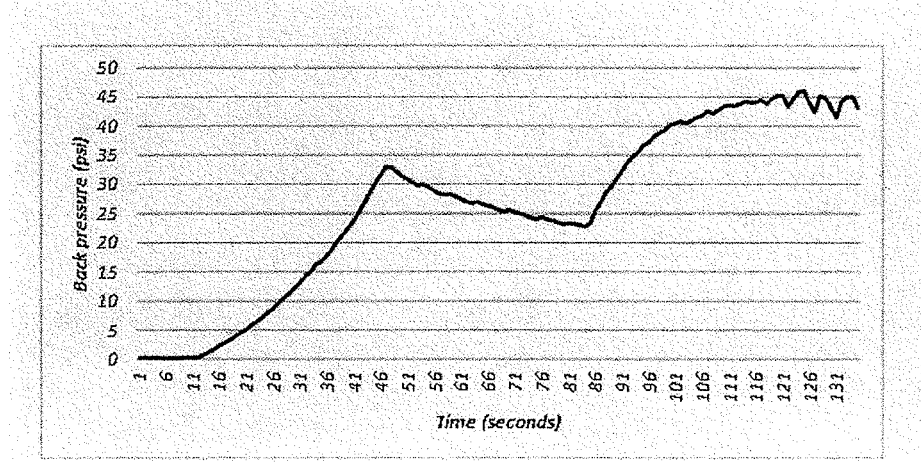
FIGS. 5F and 5G are graphs showing the effect of injector joint adjustment, on back pressure on the bevel of a needle entering the skin.
Figure 5G:
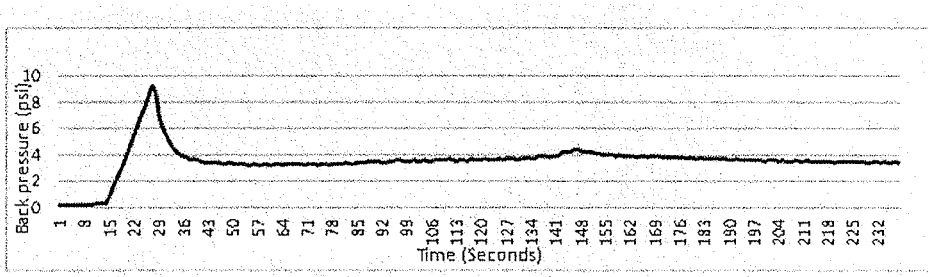

FIGS. 5F and 5G are graph that show the effect of injector joint adjustment e.g., compensation, on back pressure on the bevel of a needle resulting from a path traveled by a needle entering the skin. FIG. 5F depicts high back pressure (resistance) to an injection of an injectable into the skin resulting from a lack of adjustment e.g., compensation of a path of travel and/or angle of tilt of a needle entering the skin (also see FIG. 5D). As shown in FIG. 5F, after about 51 seconds the injection was stopped and a second attempt was made at 86 seconds. In both cases resistance to the injection increased initially exponentially between 0 psi and 33 psi and then logarithmically between 24 psi and 43-45 psi.

However, with compensation applied, as shown in FIG. 5G, a minor initial peak in backpressure between seconds 15 and 29 is followed by a low plateau throughout the injection period remaining at a level of 3-4 psi. FIGS. 5F and 5G show that proper adjustment compensation of the needle path of travel and angle of tilt when crossing the surface of skin can reduce backpressure to a level 80-85% of non-compensated needle path of travel and angle of tilt.

Figure 6A:
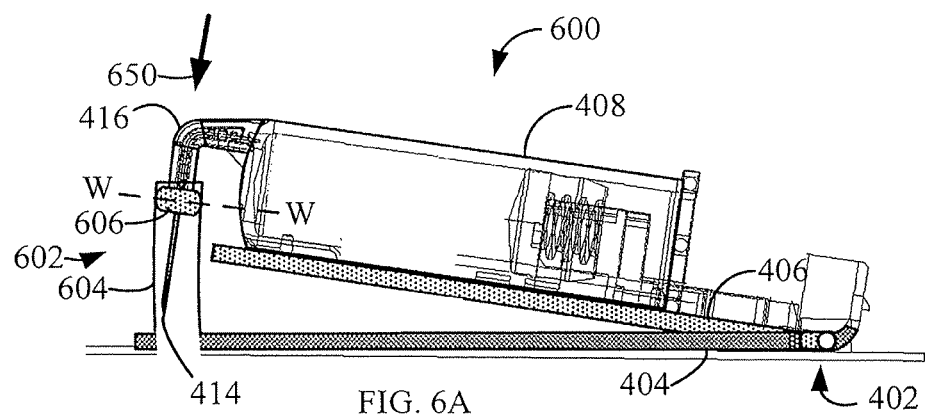
FIGS. 6A, 6B, 6C and 6D are side-view and cross-section view simplified illustrations of operative stages of an exemplary embodiment of a self-injector.
Figure 6B:
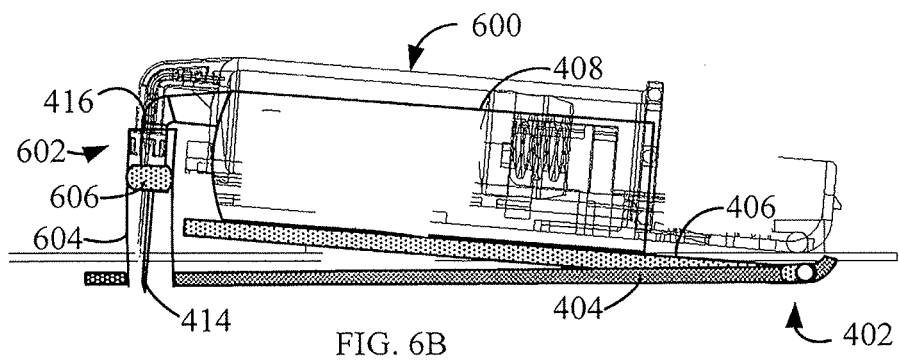
Figure 6C:
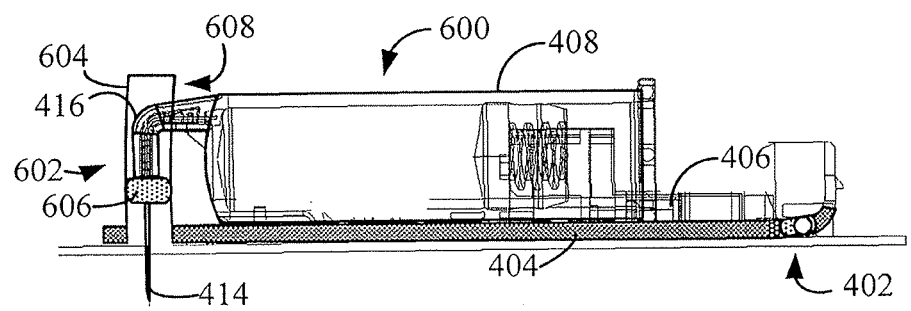
Figure 6D:
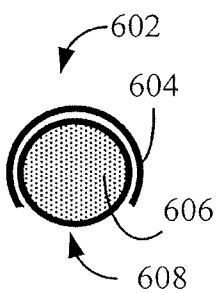

Reference is now made to FIGS. 6A, 6B and 6C, collectively referred to as FIG. 6, which are side-view partial cross section view simplified illustrations depicting three successive operative stages of an exemplary embodiment of a self-injector during introduction of a needle thereof into skin. Reference is also made to FIG. 6D, which is a cross-section view along a W-W section, simplified illustration of a joint 602 joint view from a direction indicated by arrow 650.

In some embodiments, self-injector 600 is a patch self-injector that is adhered to the surface of the skin of a user. In the exemplary embodiment of FIG. 6, self-injector 600 comprises one or more joints 602 and rotatingly connects fluid reservoir 408 and frame 404. Additionally and optionally, joint 402 rotatingly connects support plate 406 and frame 404.

In some embodiments, joint 602 comprises at least one slotted cylinder 604 coupled to frame 404 and sized to slidingly and optionally partially swivelly accommodate angled head 416 plunger 606. In some embodiments cylinder 602 is slotted along a back aspect (facing fluid reservoir 408). In some embodiments a slot 608 is fitted to allow angled head 416 freedom to move up and down cylinder 604 as self-injector 600 is rotated optionally from an elevated angular state to a final horizontal state, parallel to surface 412 of the skin. Optionally, in some embodiments, slot 608 is fitted to allow angled head 416 freedom to partially swivel within cylinder 604. In some embodiments, cylinder 602 wall is curved to slidingly accommodate both the curvilinear path of angled head 416 and needle tip 414.

As support plate 406 and fluid reservoir 408 rotate in respect to frame 404, optionally from an elevated angular state to a final horizontal state, parallel to surface 412 of the skin, plunger 606 slidingly engages cylinder 604 wall and is guided along cylinder 604 wall so that needle tip 414 approaches and eventually penetrates surface 412 of the skin, optionally moving along a tangential straight path 452, generally perpendicular to surface 412 of the skin and in a direction indicated by arrow 455. Optionally, movement of plunger 606 along curved cylinder 604 wall may result in forward movement of fluid reservoir 408 and of support plate 406 attached thereto.

In some embodiments, Plunger 606 is made of a resilient material i.e., a soft polymer or elastomer (e.g., Silicone).

Optionally, the exemplary embodiment shown in FIG. 6 may include a joint similar to joint 402 the operation thereof is explained in reference to FIG. 4 and will not be repeated.

Figure 7A:
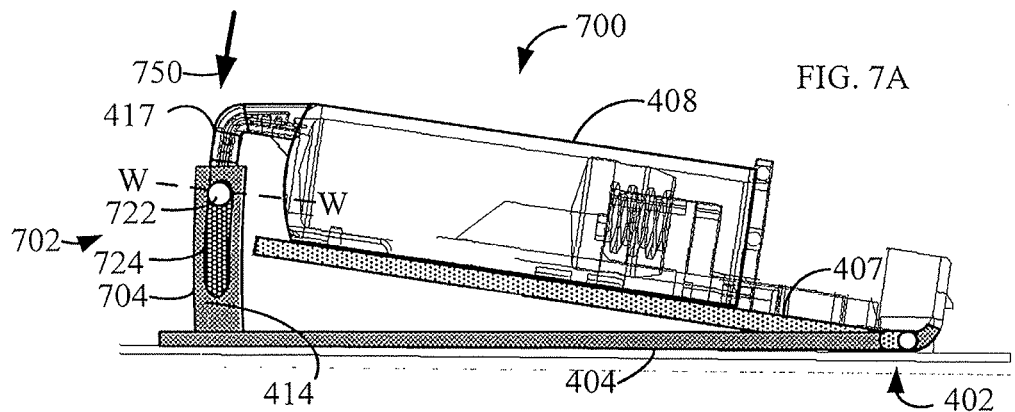
FIGS. 7A, 7B, 7C and 7D are side-view and cross-section view simplified illustrations of operative stages of an exemplary embodiment of a self-injector.
Figure 7B:
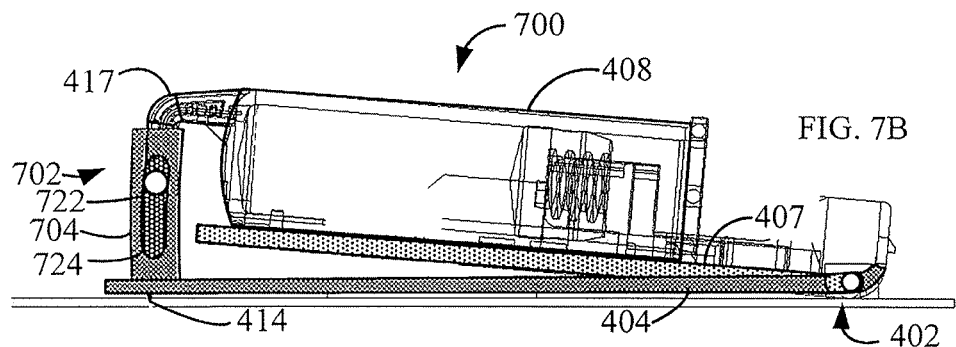
Figure 7C:
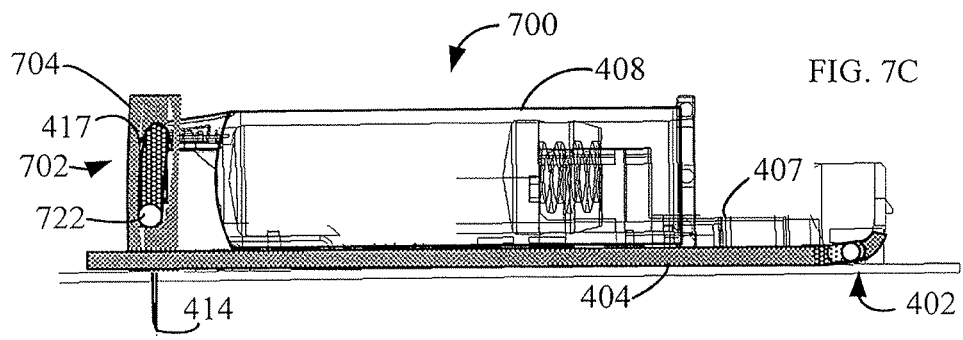
Figure 7D:
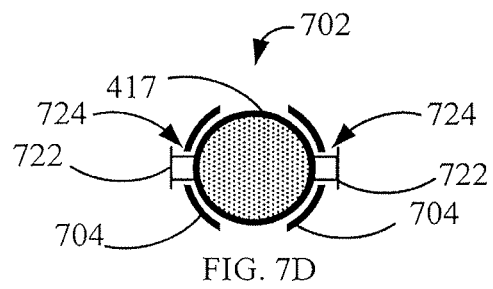

Reference is now made to FIGS. 7A, 7B and 7C, collectively referred to as FIG. 7, which are side-view simplified illustrations depicting three successive operative stages of an exemplary embodiment of a self-injector during introduction of a needle thereof into skin. Reference is also made to FIG. 7D, which is a cross-section view along a W-W section, simplified illustration of a joint 702 view from a direction indicated by arrow 750.

In some embodiments, self-injector 700 is a patch self-injector that is adhered to the surface of the skin of a user. In the exemplary embodiment of FIG. 7, self-injector 700 comprises one or more joints 702 and rotatingly connects fluid reservoir 408 and frame 404. Additionally and optionally, joint 402 rotatingly connects support plate 406 and frame 404.

In some embodiments, joint 702 comprises at least a portion of a notional cylinder wall 704 having at least one slot, coupled to frame 404 and sized to slidingly accommodate angled head 416. In the exemplary embodiment of FIG. 7, notional cylinder wall 704 comprises at least one pin 722 attached to angled head 416 and slidably engages cylinder 704 via an elongated slot 724 along notional cylinder wall 704. In the exemplary embodiment of FIG. 7, elongated slot 724 is curved to allow notional cylinder wall 704 to slidingly accommodate both the curvilinear path of angled head 416 and needle tip 414.

As support plate 406 and fluid reservoir 408 rotate in respect to frame 404, optionally from an elevated angular state to a final horizontal state, parallel to surface 412 of the skin, pin 722 slidingly engages notional cylinder wall 704 slot 724 and is guided along slot 724 so that needle tip 414 approaches and eventually penetrates surface 412 of the skin, optionally moving along a tangential straight path 452, generally perpendicular to surface 412 of the skin. Optionally, movement of pin 722 along curved slot 724 may result in forward movement of fluid reservoir 408 and of support plate 406 attached thereto.

Optionally, the exemplary embodiment shown in FIG. 7 may include a joint similar to joint 402 the operation thereof is explained elsewhere in this disclosure and will not be repeated.

Figure 8A:
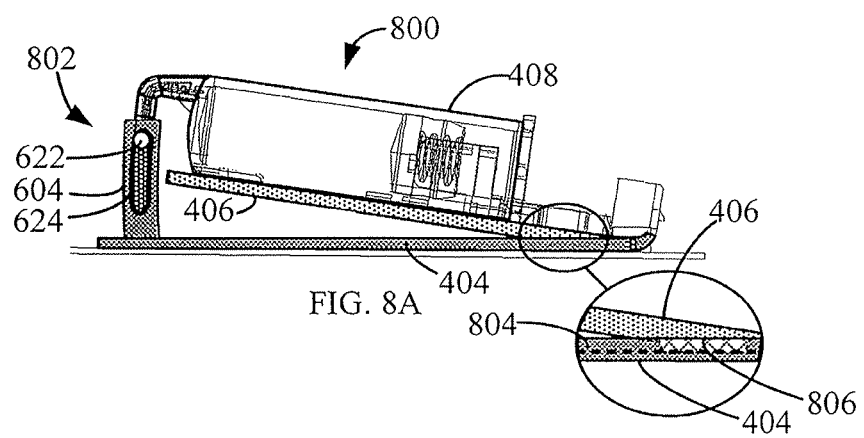
FIGS. 8A, 8B and 8C are side-view and top view simplified illustrations of exemplary embodiments of a self-injector.
Figure 8B:
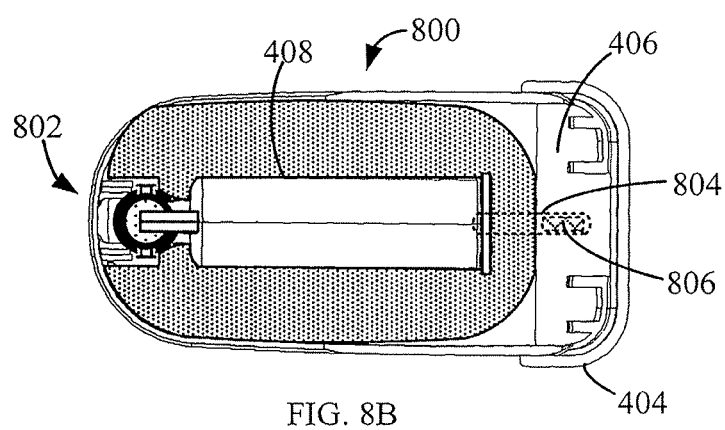

Reference is now made to FIGS. 8A, and 8B, which are side view and top view simplified illustrations of an exemplary embodiment of a self-injector. In some embodiments, self-injector 800 is a patch self-injector that is adhered to the surface of the skin of a user.

Figure 8C:
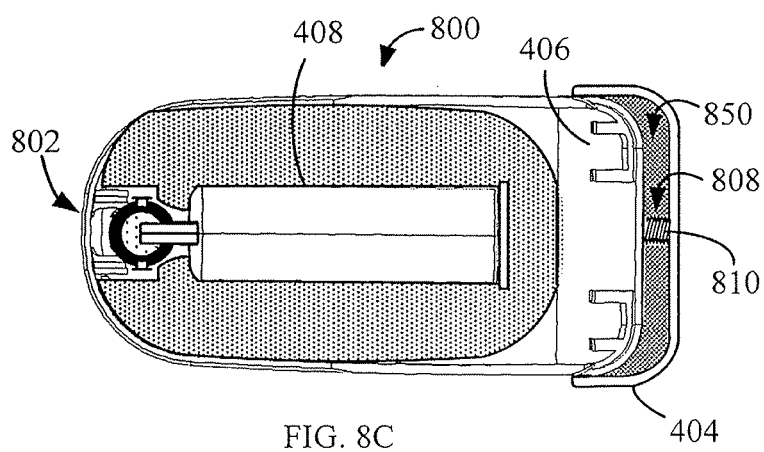

The exemplary embodiments illustrated in FIGS. 8A, 8B and 8C include a joint comprises one or more joint 802 similar to joint 702 that rotatingly connects fluid reservoir 408 and frame 404. The operation of joint 702 is explained elsewhere in this disclosure and will not be repeated.

FIGS. 8A and 8B depict an exemplary embodiment of a self-injector which comprises at least one joint 802 that comprises a groove 804 in frame 404 and a protrusion 806 attached to support plate 406 and slidingly accommodated within groove 804. In some embodiments groove 804 is in support plate 406 and protrusion 806 is attached to frame 404. In some embodiments, joint 802 is located between surfaces of frame 404 and support plate 406. In some embodiments, joint 802 is located between surfaces of frame 404 and support plate 406 that are parallel to surface 412 of the skin. In the exemplary embodiment of FIGS. 8A and 8B, protrusion 806 is in a form of a fin, however, protrusion 806 may have any geometrical shape suitable for sliding engagement with groove 804. Groove 804 is disposed parallel to the longitudinal axis of fluid reservoir 408.

As support plate 406 and fluid reservoir 408 rotate in respect to frame 404, optionally from an elevated angular state to a final horizontal state, parallel to surface 412 of the skin, protrusion 806 slidingly engages groove 804 and is guided along groove 804. In some embodiments, the width of groove 804 determines the degree at which support plate 406 is allowed to swivel in respect to frame 404 as fluid reservoir 408 and support plate 406 are pulled forward by movement of joint 602 pin 622 along curved slot 624 as explained in reference to FIG. 6.

In an exemplary embodiment, shown in FIG. 8C, injector 800 comprises at least one joint 802 similar to joint 602 that rotatingly connects fluid reservoir 408 and frame 404. The operation of joint 602 is explained elsewhere in this disclosure and will not be repeated. In some embodiments, injector 800 comprises one or more joints 808 between support plate 406 and frame 404. In some embodiments, joint 808 comprises one or more elastic members 810. In the exemplary embodiment shown in FIG. 8C the elastic member is represented by a spring.

In some embodiments, as support plate 406 and fluid reservoir 408 are rotated, optionally from an elevated angular state to a final horizontal state, parallel to surface 412 of the skin, elastic member 810 dampens forward movement as well as swivel of fluid reservoir 408 and support plate 406 relative to frame 404 as they are pulled forward by movement of joint 602 pin 622 along curved slot 624 as explained in reference to FIG. 6. In the exemplary embodiment illustrated in FIG. 8C, fluid reservoir 408 and support plate 406 are in a final horizontal state (FIG. 6C) as evident by a gap 850 formed between support plate 406 and frame 404 as a result of fluid reservoir 408 and support plate 406 has been pulled forward by joint 802.

In some exemplary embodiments joint 808 may be a spring in a compressed state when fluid reservoir 408 and support plate 406 are in their elevated angular state. In such a configuration, once the injection process is completed and fluid reservoir 408 and support plate 406 are rotated back to their elevated angular state, joint 808 elastic members 810 may assist in re-approximating fluid reservoir 408 and support plate 406 and frame 404. In some embodiments joint 808 may be a spring in a resting state when fluid reservoir 408 and support plate 406 are in their elevated angular state.

Figure 9A:
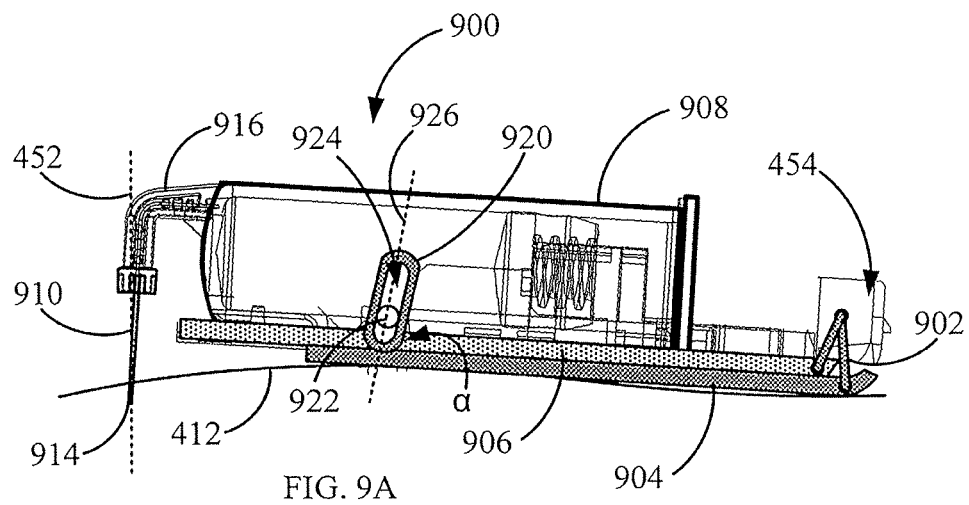
FIGS. 9A and 9B are side-view simplified illustrations of an exemplary embodiment of a self-injector in accordance with the invention.
Figure 9B:
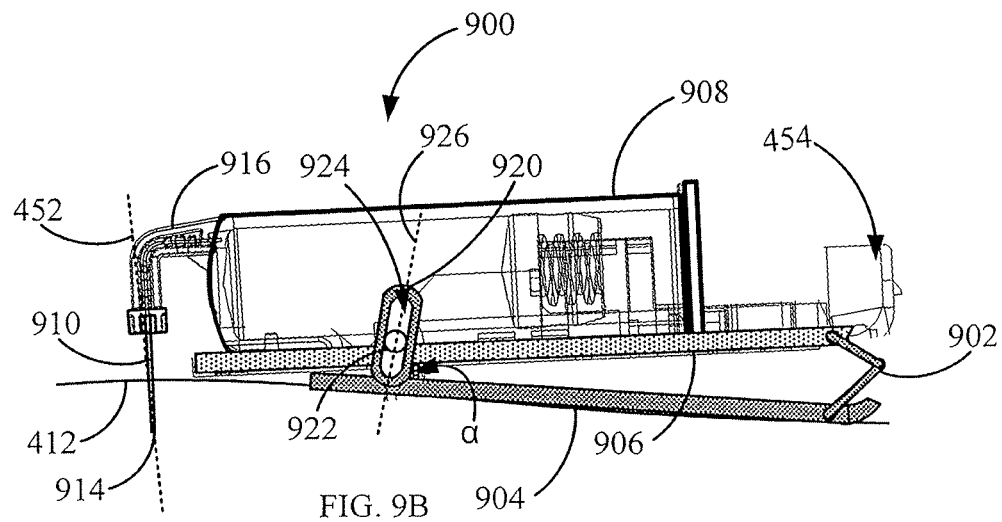

Reference is now made to FIGS. 9A and 9B, which are side view simplified illustrations of an exemplary embodiment of a self-injector. In some embodiments, self-injector 900 comprises a patch self-injector adhered to the surface of the skin of a user. In some embodiments, the self-injector comprises at least one joint 902/920 that couples a surface 904 and a fluid reservoir 908 with at least one needle 910. In some embodiments, frame surface 904 comprises a portion of a frame 906 attached to skin of a user. In some embodiments, joint 902/920 has at least one degree of freedom. In some embodiments, joint 902/920 has at least two or more degrees of freedom in respect to frame surface 904. In some embodiments, at least one of the degrees of freedom is a rotational degree of freedom, for example, rotating fluid reservoir 908 bringing needle 910 to cross surface of skin 412. In some embodiments, both degrees of freedom are on a same plane normal to skin 412. In some embodiments, at least one degree of freedom comprises translational freedom of movement, for example, moving fluid reservoir 908 and needle 910 optionally axially, in a back and forth direction [i.e., in a direction from the back end (non-needle end) towards the front end (needle-end) of injector 900 and vice versa].

In the exemplary embodiment of FIGS. 9A and 9B a fluid reservoir 908, e.g., a syringe, vial, cartridge, is supported by a support plate 906 fitted to support at least fluid reservoir 908 and at least one needle 910. In an exemplary embodiment, self-injector 900 comprises one or more joints 902/920 rotatingly connecting support plate 906 and frame 904. Joint 902 of the embodiment depicted in FIGS. 9A and 9B comprises at least one joint comprising at least two interlocking arms.

In some embodiments, support plate 906 is fitted to support at least one fluid reservoir 908 having at least one needle 910 projecting from fluid reservoir 908 angled neck 916. In some embodiments, at least a portion of needle 910 is normal to the longitudinal axis of fluid reservoir 908. In some embodiments, at least a portion of needle 910 is normal to the support plate 906.

In some embodiments injector 900 comprises at least a second joint 920 including a pin 922 attached to support plate 906 and slidably engages frame 904 via an elongated slot 924 in frame 904. Elongated slot may be in a form of a straight line, a curved line, a serpentine line, a sinusoidal line or any geometrical form calculated to bring needle 910 to travel in a straight line and enter the surface of skin 412 at a properly adjusted tilt angle (β) as described elsewhere in the disclosure.

In some embodiments, joint 920 restricts movement of joint 902. The level of restriction depends on the angle (α) between paths of translation of joints 902 and 920. In FIGS. 9A and 9B, the paths of translation of joints 902/920 are defined by elongated slot 918 in joint 920, length of one or more interlocking arms 950 and rotational limit of the pivot points coupling interlocking arms to each other and to support plate 906 and frame 904. In the exemplary embodiment of FIGS. 9A and 9B, elongated slot 924 is oriented along a forwardly declining slope 926 at an angle (α) between 40 and 90, 50 and 80, 60 and 70 degrees more than 90 or less than 40 or intermediate angles between paths of translation of joints 902 and 920. As support plate 906 is rotated about joint 902 in respect to frame 904, elongated slot 924 guides pin 922 along slope 926, which in turn pulls support plate and first joint 902 forwardly up to a limit defined by angle (α).

A potential advantage of the combined action of joints 902/920 is in the formation of a straight path of travel of needle tip 914 through surface 412 of the skin and reducing discomfort to a user during introduction of the needle into the skin.

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An injector, comprising
   at least one fluid reservoir connected to a needle;
   a surface configured for attachment to skin and coupled to said fluid reservoir by at least a first joint and a second joint, said first and second joints each being configured to permit sliding of the fluid reservoir with respect to said surface, defining a first degree of freedom for each of said first and second joints,
   wherein at least one of said first and second joints is also configured to permit a second degree of freedom with respect to said surface, said second degree of freedom being a rotational degree of freedom permitting rotation of the fluid reservoir, and
   wherein when said fluid reservoir is rotated with respect to said surface, said sliding of said fluid reservoir with respect to said surface permitted by the first and second joints concurrently with said rotation of the fluid reservoir with respect to said surface permitted by the at least one of said first and second joints, converts a curvilinear travel path of the needle into at least a portion of said needle crossing the surface within less than 5 degrees deviated from a straight line.

2. The injector according to claim 1, wherein at least a portion of a path of translation of said slidable portion of said first joint and a portion of a path of translation of said second joint are angled with respect to each another.

3. The injector according to claim 2, wherein at least a portion of said path of translation of said slidable portion of said second joint restricts said at least a portion of said path of translation of said slidable portion of said first joint.

4. The injector according to claim 2, wherein at least a portion of said path of translation of said second joint is curved.

5. The injector according to claim 4, wherein at least a portion of said needle is tangential to a curve defined by said rotational degree of freedom.

6. The injector according to claim 2, wherein when said fluid reservoir is rotated with respect to said surface, at least a portion of the travel path of at least a portion of said needle defined by at least said path of translation of said first joint and said path of translation of said second joint is configured to cross a surface of said skin along the straight line.

7. The injector according to claim 2, wherein at least a portion of at least one of said paths of translation is configured to be parallel to said skin upon attachment of the surface thereto.

8. The injector according to claim 1, wherein both degrees of freedom are on a same plane.

9. The injector according to claim 1, wherein when said fluid reservoir is rotated with respect to said surface, at least a portion of the travel path of at least a portion of said needle defined by at least said respective first and second degrees of freedom is configured to cross the surface of said skin along the straight line.

10. The injector according to claim 9, wherein said portion of said needle is the proximal edge of a bevel of said needle.

11. The injector according to claim 9, wherein a tilt angle of said needle is generally parallel to said straight line.

12. The injector according to claim 9, wherein said portion of said needle is a tip of said needle.

13. The injector according to claim 9, wherein at least said two degrees of freedom define a path of travel at which at least a portion of said needle is configured to cross the surface of said skin angled at less than 3 degrees with respect to said straight line.

14. The injector according to claim 9, wherein said portion of said needle is a tip that includes a beveled opening facing forward, away from a body of said fluid reservoir.

15. The injector according to claim 1, wherein said needle is configured to form an entry hole in skin with a diameter ($\Phi$) being twice the diameter ($\Phi'$) of said needle.

16. The injector according to claim 1, wherein at least one of said joints includes at least one pin-in-slot hinge.

17. The injector according to claim 16, wherein at least one slot is configured to be oriented parallel to the surface of the skin upon attachment of the surface thereto.

18. The injector according to claim 1, wherein at least one of said first and second joints is located between a back, non-needle end and front, needle end of the injector.

19. The injector according to claim 1, wherein said fluid reservoir further comprises at least one angled head and plunger coupled to a tip of said head and wherein at least one of said joints comprises at least one slotted cylinder coupled to said surface and sized and fitted to slidingly accommodate said angled head and said plunger.

20. The injector according to claim 1, wherein at least a portion of said needle is resilient.

21. The injector according to claim 1, wherein at least a portion of said needle is curved.

22. The injector according to claim 1, wherein at least one joint comprises at least one groove and at least one protrusion slidingly accommodated within said groove.

23. The injector according to claim 1, wherein at least one joint comprises an elastic member.

24. An injector, comprising
at least one fluid reservoir connected to a needle;
a surface configured for attachment to skin and coupled to said fluid reservoir by at least a first joint and a second joint, said first and second joints each being configured to permit sliding of the fluid reservoir with respect to said surface, defining a first degree of freedom for each of said first and second joints, and wherein at least one of said first and second joints is also configured to permit at least a second, rotational degree of freedom permitting rotation of the fluid reservoir with respect to said surface and at least one of said joints comprises at least two interlocking arms,
wherein when said fluid reservoir is rotated with respect to said surface, said sliding of said fluid reservoir with respect to said surface permitted by the first and second joints concurrently with said rotation of the fluid reservoir with respect to said surface permitted by the at least one of said first and second joints, converts a curvilinear travel path of the needle into at least a portion of said needle crossing the surface within less than 5 degrees deviated from a straight line.

25. The injector according to claim 24, wherein at least one of said interlocking arms is pivotably coupled to said surface.

26. The injector according to claim 24, wherein said interlocking arms are pivotably coupled to each other.

* * * * *